(12) United States Patent
Pardo Miro

(10) Patent No.: US 9,481,612 B2
(45) Date of Patent: Nov. 1, 2016

(54) ROOT-GROWTH-PROMOTING LIQUID FORMULATION THAT ENHANCES DEFENSE RESPONSE IN PLANTS, AND USE OF SAME

(75) Inventor: Marco Pardo Miro, Huesca (ES)

(73) Assignee: AGRO STOCK S.A., Huesca (ES)

( * ) Notice: Subject to any disclaimer, the term of this patent is extended or adjusted under 35 U.S.C. 154(b) by 49 days.

(21) Appl. No.: 14/407,479

(22) PCT Filed: Jun. 21, 2012

(86) PCT No.: PCT/ES2012/070460
§ 371 (c)(1),
(2), (4) Date: May 15, 2015

(87) PCT Pub. No.: WO2013/186405
PCT Pub. Date: Dec. 19, 2013

(65) Prior Publication Data
US 2015/0246853 A1    Sep. 3, 2015

(30) Foreign Application Priority Data

Jun. 13, 2012 (ES) .................................. 201230923

(51) Int. Cl.
| | | |
|---|---|---|
| C05F 11/10 | (2006.01) | |
| C05D 9/02 | (2006.01) | |
| C05G 3/00 | (2006.01) | |
| A01N 35/06 | (2006.01) | |
| A01G 25/02 | (2006.01) | |

(52) U.S. Cl.
CPC ............... *C05G 3/00* (2013.01); *A01G 25/023* (2013.01); *A01N 35/06* (2013.01); *C05D 9/02* (2013.01)

(58) Field of Classification Search
None
See application file for complete search history.

(56) References Cited

U.S. PATENT DOCUMENTS

| | | | | |
|---|---|---|---|---|
| 6,241,795 B1* | 6/2001 | Svec | ....................... | C05F 11/10 71/11 |
| 2004/0167028 A1* | 8/2004 | Tsuji | ....................... | A01G 7/06 504/116.1 |
| 2005/0119127 A1* | 6/2005 | Cambri | ................... | C05F 11/00 504/172 |
| 2007/0197392 A1* | 8/2007 | Takeuchi | ............... | A01N 43/36 504/287 |
| 2007/0264419 A1* | 11/2007 | Tuli | ........................ | C05G 3/00 426/651 |
| 2014/0102156 A1* | 4/2014 | Pursell | .................... | C05C 9/005 71/22 |
| 2015/0289509 A1* | 10/2015 | Garizi | ................. | C07D 401/04 504/101 |

FOREIGN PATENT DOCUMENTS

| | | |
|---|---|---|
| EP | 1538136 | 6/2005 |
| ES | 2201911 | 3/2004 |
| ES | 2332494 | 2/2010 |

OTHER PUBLICATIONS

De Linan Vicente, C. Vademecum 2001 of Productos Fitosanitarios and Nutricionales. 201, Ediciones Agrotecnicas, S. L. pp. 286-313.
Rama Rao et. al., "Menadione sodium bisulphite: A promising plant growth regulator", Plant Growth Regulation vol. 3, No. 2 (1985), pp. 111-118, 1985.
Pushpalatha, H.G. et al. Ability of Vitamins to induce downy mildew disease resistance and growth promotion in peral millet, 2007, Crop Protection, vol. 26, pp. 1674-1681, pp. 1677 and 1680.

* cited by examiner

*Primary Examiner* — Wayne Langel
(74) *Attorney, Agent, or Firm* — Defillo & Associates, Inc; Evelyn A Defillo

(57) ABSTRACT

The invention relates to a liquid formulation that stimulates the germination of seeds and the rooting of plants, including water-soluble addition compounds from the K vitamin group together with complexed microelements and essential amino acids, which acts by improving the metabolic processes that occur during the different stages in the development of treated plants, improving the appearance thereof, activating defence responses and promoting resistance to adverse conditions, both biotic and abiotic, thereby allowing harvest production and yields to be increased.

17 Claims, No Drawings

ROOT-GROWTH-PROMOTING LIQUID FORMULATION THAT ENHANCES DEFENSE RESPONSE IN PLANTS, AND USE OF SAME

CROSS REFERENCE TO RELATED APPLICATION

This application is a national stage entry of PCT/ES2012/070460 filed Jun. 21, 2012, under the International Convention claiming priority over Spain Application No. P201230923 filed Jun. 13, 2012.

TECHNICAL FIELD OF THE INVENTION

The present invention relates to a root growth promoting liquid formulation that enhances defense response in plants and to the use of same.

More particularly, the invention relates to a liquid formulation with stimulating activity for stimulating plant seed germination and root growth including water-soluble addition compounds of the vitamin K group, such as menadione sodium bisulfite (MSB), (2-methyl-1,4-naphthoquinone), menadione nicotinamide bisulfite (MNB), menadione p-aminobenzoic acid bisulfite, menadione thiamine bisulfite, menadione histidine bisulfite, menadione adenine bisulfite, menadione nicotinic acid bisulfite, menadione tryptophan bisulfite, together with complexed microelements and essential amino adds, acting by improving the metabolic processes occurring during the different stages of treated plant development, improving the appearance of plants, activating their defense responses and promoting their resistance against adverse biotic and abiotic conditions, thereby allowing increasing crop production and yield.

BACKGROUND OF THE INVENTION

It is known from the literature that the water-soluble derivative of vitamin K3 (menadione sodium bisulfite—MSB-) induces an increase in free endogenous indoleacetic acid (AIA) in plants (Rama Rao et. al., "Menadione sodium bisulphite: A promising plant growth regulator", Plant Growth Regulation Volume 3, No. 2 (1985), pp.: 111-118, 1985). Water-soluble compounds of vitamin K belong to a new class of exogenous inducers inducing plant resistance to different diseases and viruses, as well as to a number of stress factors, acting as an elicitor (exogenous activator or inducer of plant defense response) in agricultural crops under certain adverse biotic conditions and various abiotic stress factors (temperature, water, saline, etc.). Likewise, they also act as a stimulant for certain metabolic reactions in plants that are basic for growth and development as well as for adaptation and resistance to various stress factors.

In this sense, patent document ES2201911 entitled "Uso de composiciones quo contienen menadiona y/o alguno(s) de sus derivatives para bioestimular los mecanismos naturales de defensa de las plantas, a fin de contrarrestar entre otros los daños producidos por pesticidas y herbicidas (Use of compositions containing menadione and/or one or more derivatives thereof for the biostimulation of the natural defense mechanisms of plants in order to counteract, for example, damage caused by pesticides and herbicides)", for example, describes aqueous solutions which can contain, individually or jointly, vitamin K3 as active components, the soluble derivatives thereof [preferably menadione sodium bisulfite or MSB] or sparingly soluble derivatives thereof [preferably menadione nicotinamide bisulfite or MNB], with respective concentrations comprised between 0.0001 and 200 ppm, 0.001 and 10000 ppm, 0.001 and 10000 ppm, preferably vitamin K3 between 0.001 and 100 ppm, MSB between 0.01 and 5000 ppm, MNB between 0.01 and 5000 ppm, for application in agriculture and horticulture, preferably by spraying the aerial part of the plant or by the irrigation system, being able to be mixed with various additives, such as organic and inorganic fertilizers, insecticides, nematicides, fungicides, bactericides or herbicides.

Patent document ES 2332494 B1 entitled "Uso de menadiona para aumentar la tolerancia al estrés salino de as plantas (Use of menadione to increase saline stress tolerance in plants)" relates to the use of an aqueous composition comprising menadione and/or one or more water-soluble derivatives thereof for inducing saline stress tolerance in plants and/or seeds, where the aqueous composition particularly comprises $3.3 \times 10^{-7}$ to 0.66 mM of menadione (Vitamin K3), $3.3 \times 10^{-6}$ to 33.3 mM of a water-soluble derivative of vitamin K3 which is a bisulfite selected from menadione sodium bisulfite (MSB), menadione potassium bisulfite, menadione ammonium bisulfite or menadione magnesium bisulfite; $3.3 \times 10^{-5}$ to 33.3 mM of a poorly water-soluble derivative of vitamin K3 which is a bisulfite selected from menadione nicotinamide bisulfite (MNB), menadione p-aminobenzoic add bisulfite, menadione histidine bisulfite, menadione adenine bisulfite, menadione nicotinic add bisulfite or menadione tryptophan bisulfite; or any combination of the compositions according to (a), (b) and/or (c).

Patent document EP 1538136 B1 entitled "Fertilizer composition to stimulate the absorption of nutritive substances in plants" relates to a composition comprising a mixture of vitamin K and/or derivatives thereof, alginic acid and/or derivatives thereof and betaine.

SUMMARY OF THE INVENTION

An object of the present invention is to provide a liquid formulation with stimulating activity for stimulating plant seed germination and root growth including water-soluble addition compounds of vitamin K, together with complexed microelements and essential amino acids allowing synergistic action of the three essential elements by increasing the capacity to absorb the complexed microelements supplied thereto as a result of the capacity to chelate same, as well as greater mobilization of such microelements in the plant, allowing said microelements to be assimilated quickly, effectively and in a large amount and promoting their arrival at the sites where they must perform their action, together with the action of vitamin K, activating the defense responses of the plant, such that it allows the plant to respond to attacks by both biotic and abiotic agents in a natural and more effective manner. The vitamin K eliciting and activating action with respect to natural plant defense mechanisms is due in part to increased endogenous indoleacetic acid levels in plants together with an increased biosynthesis of phytoalexins and of different types of defensive-antioxidant proteins. This biosynthesis of proteins is promoted by supplying complexed microelements. Furthermore, vitamin K enhances the absorption of such microelements, resulting in a significant improvement of the appearance of plants and their fruits, with a subsequent result in crop production.

DESCRIPTION OF THE INVENTION

The liquid formulation of the invention includes between 5 and 15% of zinc, between 3 and 10% of manganese, between 1 and 3% of boron, between 3 and 3.5% of copper, between 0.1 and 1.0% of water-soluble addition compounds of the vitamin K group and between 3 and 8% of complex of essential amino acids, in percentages by weight with respect to the final liquid formulation.

In one embodiment of the invention, zinc is supplied to the formulation in the form of zinc (II) sulfate heptahydrate in a proportion of 22.54%, manganese is supplied in the form of manganese (II) sulfate in a proportion of 32%, boron is supplied in the form of boric acid in a proportion of 16%, and copper is supplied in the form of copper (II) sulfate in a proportion of 25%, all the percentages being expressed with respect to 100% of the weight of the final formulation.

The complex of amino acids is preferably selected from proline, glycine, alanine and combinations thereof.

The formulation of the invention includes a dispersing agent, preferably lignosulfonate, which also acts as a complexing agent for complexing the cations included in the formula (Mn, Zn, Cu).

In a preferred embodiment of the invention, the liquid formulation includes between 10 and 25% of lignosulfonate, between 5 and 15% of zinc (II) sulfate heptahydrate, between 3 and 10% of manganese (II) sulfate, between 1 and 3% of boric acid, between 1 and 4% of copper (II) sulfate, between 0.1 and 1.0% of water-soluble addition compounds of vitamin K and between 3 and 8% of the complex of amino acids, the rest, up to 100% of the weight of the liquid formulation, being water.

In this regard, manganese is an essential microelement for plants since it catalyzes respiratory reactions of nitrogen metabolism, phosphatic acid synthesis and photosynthesis, and it intervenes in enzymatic reactions of the carbonic acid cycle and provides stability to chloroplasts. Zinc in turn is the essential component of a number of dehydrogenases, proteinases and peptidases. It intervenes in the respiratory process in the form of carbonic anhydrase. It stabilizes cytoplasm structure and intervenes in protein synthesis. Zinc deficiency seems to be accompanied by a drastic reduction in RNA, in the number of ribosomes in cells, and in the stability thereof. It also seems to be involved in tryptophan and indoleacetic acid synthesis. Boron promotes sugar transport through membranes, regulates phenol content and is involved in the auxin mechanism. Generally, it stimulates tissue growth in the cambium and apical meristems and promotes pollen production and fertilization. Copper acts as a catalyst for a number of enzymatic reactions and is part of the prosthetic group of a number of proteins such as ascorbic acid, phenol or cytochrome oxidases and oxidases of the electron transport system in photosynthesis. It promotes nitrogen use and protein synthesis and acts as a chlorophyll stabilizer.

Another object of the invention is the use of the formulation described above for stimulating plant seed germination and root growth, for improving the metabolic processes occurring during the different stages of plant development, for improving the appearance of plants and their fruits, for activating their defense responses and for promoting resistance against adverse biotic and abiotic conditions, thereby increasing crop production and yield.

In a preferred use of the formulation of the invention, said formulation is incorporated in the ground by means of fertigation, in drip irrigation, spray irrigation or by distributing it in areas close to the plant in surface irrigation, in the initial phases of development, for stimulating new root formation. In this embodiment, the formulation dose to be used is 10 to 40 liters per hectare of crop.

In another preferred use, the seeds, for example rice seeds, are submerged in the diluted formulation to speed up germination and sprouting of roots. In this embodiment, the dose to be used is between 1 to 10 grams of formulation per kilogram of seeds.

Another preferred use is by means of foliar applications on plants with a suitable volume of water to cover the surface of the plants.

EXAMPLE 1

A test of the product of the invention was carried out on corn to be used for making popcorn, this variety being chosen because it is a crop in which the first stages of development are characterized by vegetative and root growth difficulty.

To that end, this variety of corn was planted and the crop was divided into three areas. A few days after planting, no root growth promoting product whatsoever was applied in one of said areas (control), an amino acid-based commercial product of this type was applied in another partition at a ratio of 20 l/ha, and finally, the product of the invention was applied in a third partition in the same ratio of 20 l/ha. The results obtained are shown in the following table:

| Treatment with | | Without treatment |
| --- | --- | --- |
| Product of the invention | Commercial product | Control |
| 8344 kg/ha (dry) | 7856 kg/ha (dry) | 3741 kg/ha (dry) |

The results demonstrate that production in the partition where the product of the invention was applied exceeded the production corresponding to the control partition by about 24% and the production corresponding to the partition treated with the commercial product by 16%.

EXAMPLE 2

In view of the results obtained in Example 1, a test was carried out only with the product of the invention in three different plots in order to check if there was a dosage-production relationship when using the product of the invention. To that end, the product of the invention was applied in two plots at a ratio of 20 l/ha and 30 l/ha, respectively, the third plot being left untreated. The results are shown in the following table:

| Treatment with the product of the invention | | Without treatment (control) |
| --- | --- | --- |
| 20 l/ha | 30 l/ha | — |
| 8193 kg/ha (dry) | 8230 kg/ha (dry products) | 6730 kg/ha (dry) |

The rising trend in the productions of the plots where the product of the invention is applied is confirmed. The increase in production with respect to the control is in the order of 21% and 22%, respectively, there being no significant response to the increase in treatment dose.

EXAMPLE 3

A test of the product of the invention was carried out on corn to be used for making popcorn, in this case two plots where the ground has a poor structure and certain salinity being selected. A few days after planting, no root growth promoting product whatsoever was applied in one of said plots (control) and the product of the invention was applied in the other plot in a ratio of 20 l/ha. The results obtained are shown in the following table:

| Treatment with the product of the invention 20 l/ha | Without treatment (control) |
|---|---|
| 6980 kg/ha | 5885 kg/ha |

The results show a positive difference of 1095 kg/ha in the treated plot, which involves a production increase of 18.6%.

The invention claimed is:

1. A liquid formulation with a stimulating activity for a stimulating plant seed germination and a root growth comprising:
   a water-soluble addition compound of a vitamin K group selected from the group consisting of menadione sodium bisulfite (MSB), 2-methyl-1,4-naphthoquinone, menadione nicotinamide bisulfite (MNB), menadione p-aminobenzoic acid bisulfite, menadione thiamine bisulfite, menadione histidine bisulfite, menadione adenine bisulfite, menadione nicotinic acid bisulfite, and menadione tryptophan bisulfite;
   complexed microelements of zinc, manganese, copper and boron;
   a complex of essential amino acids selected from the group consisting of proline, alanine, glycine, and combinations thereof; and
   water;
   wherein the liquid formulation includes:
   between 5% and 15% weight of zinc;
   between 3 and 10% weight of manganese;
   between 1 and 3% weight of boron;
   between 3 and 3.5% weight of copper;
   between 0.1 and 1.0% weight of said water-soluble addition compound of the vitamin K group; and
   between 3 and 8% weight of the complex of essential amino acids;
   the remaining being water.

2. The liquid formulation according to claim 1, wherein the zinc is zinc sulfate heptahydrate.

3. The liquid formulation according to claim 1, wherein the manganese is manganese sulfate.

4. The liquid formulation according to claim 1, wherein the boron is boric acid.

5. The liquid formulation according to claim 1, wherein the copper is copper (II) sulfate.

6. The liquid formulation according to claim 2, wherein the formulation has between 5 and 15% of zinc (II) sulfate heptahydrate.

7. The liquid formulation according to claim 3, wherein the formulation has between 3 and 10% of manganese (II) sulfate.

8. The liquid formulation according to claim 4, wherein the formulation has between 1 and 3% of boric acid.

9. The liquid formulation according to claim 5, wherein the formulation has between 1 and 4% of copper (II) sulfate.

10. A liquid formulation with a stimulating activity for a stimulating plant seed germination and a root growth, the liquid formulation comprising:
    a water-soluble addition compound of a vitamin K group selected from the group consisting of menadione sodium bisulfite (MSB), 2-methyl-1,4-naphthoquinone, menadione nicotinamide bisulfite (MNB), menadione p-aminobenzoic acid bisulfite, menadione thiamine bisulfite, menadione histidine bisulfite, menadione adenine bisulfite, menadione nicotinic acid bisulfite, and menadione tryptophan bisulfite;
    complexed microelements of zinc, manganese, copper and boron;
    a complex of essential amino acids selected from the group consisting of proline, alanine, glycine, and combinations thereof;
    water; and
    lignosulfonate as a dispersing and a complexing agent.

11. The liquid formulation according to claim 10, wherein the lignosulfonate is present in a proportion of 10 to 25% by weight with respect to the formulation.

12. A method for stimulating a plant seed germination and a root growth, for improving metabolic processes occurring during different stages of a plant development, for improving an appearance of plants and their fruits, for activating their defense responses, and for promoting a resistance against adverse biotic and abiotic conditions, the method including the step of incorporating into the ground the liquid formulation according to claim 1.

13. The method according to claim 12, wherein the liquid formulation is incorporated in the ground by fertigation, drip irrigation, spray irrigation, or by distributing the liquid formulation in areas close to the plant in surface irrigation.

14. The method according to claim 13, wherein the liquid formulation is used at a dose of 20 to 30 liters per hectare.

15. The method according to claim 12, wherein the seeds are submerged in a diluted formulation.

16. The method according to claim 15, wherein a dose of 1 to 10 grams of the diluted formulation is used per kilogram of seeds.

17. The method according to claim 12, wherein the liquid formulation is incorporated into the plant by foliar applications.

* * * * *